(12) United States Patent
Hartley (10) Patent No.: US 9,050,181 B2
(45) Date of Patent: *Jun. 9, 2015

(54) RING STENT

(75) Inventor: David Ernest Hartley, Wannanup (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/278,790

(22) Filed: Oct. 21, 2011

(65) Prior Publication Data

US 2012/0035710 A1    Feb. 9, 2012

Related U.S. Application Data

(63) Continuation of application No. 10/962,638, filed on Oct. 12, 2004, now Pat. No. 8,043,357.

(60) Provisional application No. 60/510,242, filed on Oct. 10, 2003.

(51) Int. Cl.
| | |
|---|---|
| *A61F 2/06* | (2013.01) |
| *A61F 2/07* | (2013.01) |
| *A61F 2/86* | (2013.01) |
| *A61F 2/92* | (2013.01) |
| *A61F 2/915* | (2013.01) |
| *A61F 2/89* | (2013.01) |
| *A61F 2/90* | (2013.01) |

(52) U.S. Cl.
CPC ... *A61F 2/07* (2013.01); *A61F 2/86* (2013.01); *A61F 2/92* (2013.01); *A61F 2002/075* (2013.01); *A61F 2002/91591* (2013.01); *A61F 2/89* (2013.01); *A61F 2/90* (2013.01); *A61F 2220/0016* (2013.01); *A61F 2220/0075* (2013.01)

(58) Field of Classification Search
CPC .............. A61F 2/07; A61F 2/90; A61F 2/89; A61F 2/86; A61F 2002/825; A61F 2002/91558; A61F 2002/91575; A61F 2/92
USPC .............. 623/1.11–1.54, 2.36, 2.38; 606/191, 606/194, 198, 200, 153, 155, 108
See application file for complete search history.

(56) References Cited

U.S. PATENT DOCUMENTS

| | | | |
|---|---|---|---|
| 4,856,516 A | * | 8/1989 | Hillstead ........................ 606/194 |
| 4,907,336 A | | 3/1990 | Gianturco ........................ 29/515 |
| 5,242,452 A | | 9/1993 | Inoue .............................. 606/108 |

(Continued)

FOREIGN PATENT DOCUMENTS

WO    WO 98/53761    12/1998

OTHER PUBLICATIONS

Office Action filed in corresponding U.S. Appl. No. 10/962,638 on Oct. 11, 2006 (8 pages).

(Continued)

*Primary Examiner* — Katherine M Shi
(74) *Attorney, Agent, or Firm* — Brinks Gilson & Lione (57) ABSTRACT

A stent arrangement which has at least a first ring (3) and zig zag struts (5) extending axially from the periphery of the ring. There can be first and second rings (3, 4) axially spaced apart and defining substantially parallel planes and a plurality of zig zag portions (5) between the first and second ring portions around the periphery thereof. The stent can be formed from a single wire or laser cut from a cannula and can be covered or uncovered.

16 Claims, 9 Drawing Sheets

(56) References Cited

U.S. PATENT DOCUMENTS

| | | | |
|---|---|---|---|
| 5,282,824 A | 2/1994 | Gianturco | 606/198 |
| 5,290,305 A * | 3/1994 | Inoue | 623/1.2 |
| 5,354,308 A | 10/1994 | Simon et al. | 606/198 |
| 5,387,235 A | 2/1995 | Chuter | 623/1 |
| 5,397,351 A * | 3/1995 | Pavcnik et al. | 623/2.35 |
| 5,554,181 A * | 9/1996 | Das | 623/1.12 |
| 5,720,776 A | 2/1998 | Chuter et al. | 623/1 |
| 6,187,036 B1 * | 2/2001 | Shaolian et al. | 623/1.15 |
| 6,206,931 B1 | 3/2001 | Cook et al. | 623/23.75 |
| 6,287,336 B1 * | 9/2001 | Globerman et al. | |
| 6,383,216 B1 | 5/2002 | Kavteladze et al. | 623/1.22 |
| 6,524,335 B1 | 2/2003 | Hartley et al. | 623/1.13 |
| 6,616,675 B1 | 9/2003 | Evard et al. | 606/155 |
| 6,635,080 B1 * | 10/2003 | Lauterjung et al. | 623/1.13 |
| 6,641,609 B2 * | 11/2003 | Globerman | 623/1.15 |
| 6,939,370 B2 | 9/2005 | Hartley et al. | 623/1.11 |
| 6,974,471 B2 | 12/2005 | Van Schie et al. | 623/1.12 |
| 2001/0010015 A1 | 7/2001 | Hijlkema | 623/1.16 |
| 2003/0033003 A1 | 2/2003 | Harrison et al. | 623/1.15 |
| 2003/0120332 A1 | 6/2003 | Hartley | 623/1.13 |
| 2003/0233140 A1 | 12/2003 | Hartley et al. | 623/1.11 |
| 2004/0054396 A1 | 3/2004 | Hartley et al. | 623/1.13 |
| 2004/0073289 A1 | 4/2004 | Hartley | 623/1.13 |
| 2004/0082990 A1 | 4/2004 | Hartley | 623/1.13 |
| 2004/0106978 A1 | 6/2004 | Greenberg et al. | 623/1.13 |
| 2004/0147997 A1 * | 7/2004 | Gittings | 623/1.11 |
| 2006/0136031 A1 | 6/2006 | Gallo et al. | 623/1.11 |

OTHER PUBLICATIONS

Amendment and Response to First Office Action filed in corresponding U.S. Appl. No. 10/962,638 on Dec. 26, 2006 (6 pages).

Office Action filed in corresponding U.S. Appl. No. 10/962,638 on Mar. 12, 2007 (7 pages).

Amendment and Response to Final Office Action filed in corresponding U.S. Appl. No. 10/962,638 on Apr. 18, 2007 (7 pages).

Advisory Action filed in corresponding U.S. Appl. No. 10/962,638 on May 22, 2007 (3 pages).

Amendment and Response Lodged Along with RCE filed in corresponding U.S. Appl. No. 10/962,638 on Jun. 12, 2007 (8 pages).

Office Action filed in corresponding U.S. Appl. No. 10/962,638 on Sep. 12, 2007 (8 pages).

Amendment and Response to Office Action filed in corresponding U.S. Appl. No. 10/962,638 on Nov. 29, 2007 (8 pages).

Office Action filed in corresponding U.S. Appl. No. 10/962,638 on Apr. 2, 2008 (11 pages).

Response to Final Office Action filed in corresponding U.S. Appl. No. 10/962,638 on May 23, 2008 (10 pages).

Advisory Action filed in corresponding U.S. Appl. No. 10/962,638 on Jun. 5, 2008 (3 pages).

Amendment and Response to Office Advisory Action filed in corresponding U.S. Appl. No. 10/962,638 on Jul. 1, 2008 (7 pages).

Office Action filed in corresponding U.S. Appl. No. 10/962,638 on Sep. 3, 2008 (7 pages).

Response to Office Action filed in corresponding U.S. Appl. No. 10/962,638 on Nov. 14, 2008 (5 pages).

Office Action filed in corresponding U.S. Appl. No. 10/962,638 on Feb. 3, 2009 (7 pages).

Response to Final Office Action filed in corresponding U.S. Appl. No. 10/962,638 on Apr. 3, 2009 (5 pages).

Advisory Action filed in corresponding U.S. Appl. No. 10/962,638 on Apr. 29, 2009 (3 pages).

Amendment and Response to Advisory Action filed in corresponding U.S. Appl. No. 10/962,638 on May 6, 2009 (5 pages).

Office Action filed in corresponding U.S. Appl. No. 10/962,638 on May 19, 2009 (6 pages).

Amendment and Response to Office Action filed in corresponding U.S. Appl. No. 10/962,638 on Aug. 19, 2009 (6 pages).

Office Action filed in corresponding U.S. Appl. No. 10/962,638 on Jan. 12, 2010 (7 pages).

Response to Final Office Action filed in corresponding U.S. Appl. No. 10/962,638 on Mar. 11, 2010 (5 pages).

Office Action filed in corresponding U.S. Appl. No. 10/962,638 on Apr. 12, 2010 (7 pages).

Response to Final Office Action filed in corresponding U.S. Appl. No. 10/962,638 on Jun. 3, 2010 (5 pages).

Advisory Action filed in corresponding U.S. Appl. No. 10/962,638 on Jun. 16, 2010 (3 pages).

Response to Advisory Action filed in corresponding U.S. Appl. No. 10/962,638 on Jul. 12, 2010 (4 pages).

Advisory Action filed in corresponding U.S. Appl. No. 10/962,638 on Jul. 21, 2010 (3 pages).

Pre-Appeal Brief Request for Review filed in corresponding U.S. Appl. No. 10/962,638 on Aug. 3, 2010 (6 pages).

Notice of Panel Decision from Pre-Appeal Brief Request for Review filed in corresponding U.S. Appl. No. 10/962,638 on Aug. 31, 2010 (2 pages).

Appeal Brief (Corrected) filed in corresponding U.S. Appl. No. 10/962,638 on Apr. 13, 2011 (28 pages).

Notice of Allowance filed in corresponding U.S. Appl. No. 10/962,638 on Sep. 27, 2011 (7 pages).

\* cited by examiner

RING STENT

CROSS-REFERENCE TO RELATED APPLICATIONS

The present patent document is a continuation application that claims the benefit of priority under 35 U.S.C. §120 of U.S. patent application Ser. No. 10/962,638, filed Oct. 12, 2004 now U.S. Pat. No. 8,043,357, which claims priority under 35 U.S.C. §119(e) to U.S. Provisional Patent Application Ser. No. 60/510,242 filed Oct. 10, 2003, each of which are hereby incorporated by reference in their entirety.

TECHNICAL FIELD

This invention relates to a medical device and in particular to a stent for endovascular and endoluminal vessel repair and support.

BACKGROUND OF THE INVENTION

Stents are used in surgical procedures to repair or support a body lumen. Stents may be balloon expandable or may be self expanding. That is, stents may be formed from a ductile material and be supplied in a contracted or reduced diameter form to enable deployment to a target lumen and then expanded to a larger diameter by the use of a balloon. In another form a stent may be formed from a resilient material and be supplied in a diametrically or radially constrained form for delivery and then expanded when radial constraint is removed. Such stents may be covered or uncovered.

Stents proposed by Gianturco (U.S. Pat. No. 5,035,706) have a closed zig zag configuration comprising struts and bends between the struts. These stents do not have good dimensional stability because when formed into a cylindrical stent, unless constrained, their diameter is not fixed. This means that in some situations, a stent may put more outwardly radial pressure on a vessel than is desirable or it may not be easy to seal a stent graft within such a cylindrical stent.

SUMMARY OF THE INVENTION

In one illustrative and preferred embodiment therefore, the invention is said to reside in a stent arrangement comprising a first ring and a second ring, the second ring being substantially parallel to and spaced axially apart from the first ring and a plurality of zig zag portions extending between and around the peripheries of the first and second ring.

It is the object of this invention to provide a self expanding stent which has good dimensional stability.

All of the first ring, second ring and the zig zag portions can be from a portion of wire or a single piece of wire. Preferably the wire is a resilient wire.

Preferably each zig zag portion is formed by struts with a bend between adjacent struts. The bend in between the adjacent struts may include a helix arrangement to put more resiliency into each bend.

Alternatively each zig zag portion is formed by two struts with a bend, a circumferential portion and another bend between adjacent struts. In this arrangement the circumferential portion forms part of the respective ring which makes the attachment of the ring to a portion of graft material, as discussed below, more secure.

The bends between the struts may be adjacent the rings or incorporate one of the rings into the angle of the bend.

Preferably there are first and second turns of wire in each of the first ring and the second ring.

The terminal end of the wire in each of the first ring and the second ring is preferably provided with a loop so that the stent does not present a pointed end of wire which could damage a vessel.

Preferably the at least one ring is a first ring and adjacent alternate bends of the zig zag portion and a second ring is spaced apart from the first ring and adjacent an opposite bend of the zig zag portion and there are at least two turns of wire in the second ring and a terminal end of the wire in the second ring is provided with a loop so that the stent does not present a pointed end of wire which could damage a vessel.

In a preferred embodiment, the stent may be produced with first and second turns of the wire for the first ring, at least three zig zag pairs of struts extending around the periphery of the ring, a strut extending to the second ring and then at least three pairs of zig zag struts around the periphery of the second ring and extending back towards the first ring and then at least two turns of the wire for the second ring.

The wires are preferably made of stainless steel, nitinol or other resilient wire.

The stent, which when completed, is in a substantially cylindrical or drum form, may be covered or lined with a bio-compatible graft material or may be used un-lined.

The bio-compatible graft material can include polytetrafluoroethylene, Dacron, Thoralon™, polyamide or any other suitable biocompatible graft material.

While Dacron, expanded polytetrafluoroethylene (ePTFE), Thoralon™, or other synthetic biocompatible materials can be used for the tubular graft material for the stent graft, a naturally occurring biomaterial, such as collagen, is highly desirable, particularly a specially derived collagen material known as collagenous extracellular matrix (ECM) material, such as small intestinal submucosa (SIS). Besides SIS, examples of ECM's include pericardium, stomach submucosa, liver basement membrane, urinary bladder submucosa, tissue mucosa, and dura mater.

SIS is particularly useful, and can be made in the fashion described in Badylak et al., U.S. Pat. No. 4,902,508; Intestinal Collagen Layer described in U.S. Pat. No. 5,733,337 to Carr and in 17 Nature Biotechnology 1083 (November 1999); Cook et al., WIPO Publication WO 98/22158, dated 28 May 1998, which is the published application of PCT/US97/14855, the teachings of which are incorporated herein by reference. Irrespective of the origin of the material (synthetic versus naturally occurring), the material can be made thicker by making multilaminate constructs, for example SIS constructs as described in U.S. Pat. Nos. 5,968,096; 5,955,110; 5,885,619; and 5,711,969. In addition to xenogenic biomaterials, such as SIS, autologous tissue can be harvested as well, for use in forming the tubular graft material. Additionally Elastin or Elastin-Like Polypetides (ELPs) and the like offer potential as a material to fabricate the tubular graft material to form a device with exceptional biocompatibility.

SIS is available from Cook Biotech, West Lafayette, Ind., USA.

To assist with radial compressibility, each of the first and second rings may be made in a "wavy" form with the apices of the waves extending towards the other ring.

A stent according to this invention may be used at the ends of legs or arms of stent grafts to give dimensional stability where such arms or legs engage against the wall of a vessel. The stent can also be used as a short extension affixed to and extending from a fenestration in a stent graft to provide a good sealing and dimensionally stable surface for an extension arm from the fenestrated stent graft.

The stents according to this invention may be "piggy backed" or stacked with sequential rings and zig zags to make a longer tubular stent.

In one embodiment the rings and struts of the ring stent can be, for instance, laser cut from a metallic tube or cannula in a well known manner or commercially obtained from a number of stent manufacturers. The metal may be suitably heat treated to make it deformable and resilient.

The stents according to this invention may be manufactured in diameters of from 3 mm to 40 mm and lengths of from 3 mm to 40 mm. Preferably the diameter ranges from about half the length to twice the length and more preferably the diameter is about the same as the length.

The wire from which the stent in one form may be formed may have a diameter or thickness of from approximately 35 microns to approximately 500 microns. Where the stent is formed by laser cutting from a metal tube the diameter of the metal tube may have a diameter of from 3 mm to 40 mm and have a wall thickness of from about 35 microns to about 500 microns.

In a further form the invention may be said to reside in a stent arrangement comprising at least one of a first resilient ring and a second resilient ring, the second ring defining a plane which is substantially parallel to and spaced axially apart from the plane of the first ring and a plurality of zig zag portions extending between and around the periphery of a least one of the first ring and second ring.

Preferably at least one of the first ring and the second ring comprises a metallic material.

Preferably at least one of the first ring and the second ring is formed from a wire or a metal cannula.

The or each ring and the zig zag portions may be formed from a single piece of wire.

Each zig zag portion may be formed by struts with a bend between adjacent struts.

The bends between the struts may be adjacent the or each ring.

Preferably there are two turns of wire or metal cannula in each of the first ring and second ring.

A terminal end of the wire in the or each ring may be provided with a loop so that the stent does not present a pointed end of wire or metal cannula which could damage a vessel.

The at least one ring may be adjacent alternate bends of the zig zag portion and a second ring may be spaced apart from the first ring and in a parallel plane and adjacent the opposite bend of the zig zag portion.

In a further form, the invention is said to reside in a stent arrangement comprising first and second ring portions axially spaced apart and a plurality of zig zag portions between the first and second ring portions around the periphery thereof.

Preferably, each zig zag portion is formed by first and second struts with a bend in between them.

In a further form, the invention is said to reside in a stent formed from a single piece of resilient wire, the stent comprising, in order along the wire, at least one first circle or turn of the wire, a first set of zig zag struts around the periphery of the first turn wire, a strut to a position spaced axially from the first turn, a second set of zig zag struts around the periphery of the first turn and at least one second circle or turn of the wire.

The second circle or turn of wire is preferably substantially co-planar with the first circle or turn of wire.

In an alternative form the invention is said to reside in a stent arrangement comprising at least one ring formed from a portion of wire and a plurality of zig zag portions extending axially from and around the periphery of the ring.

The or each ring and the zig zag portions are preferably formed from a single piece of wire and each zig zag portion is formed by struts with a bend between adjacent struts. Preferably the bends between the struts are adjacent the or each ring.

In one embodiment there are two turns of wire in the or each ring. A terminal end of the wire in the or each ring may be provided with a loop so that the stent does not present a pointed end of wire which could damage a vessel.

In a further form the invention is said to reside in a stent arrangement comprising a first ring formed from a portion of wire, a second ring formed from a portion of wire, the second ring defining a plane which is substantially parallel to and spaced axially apart from the plane of the first ring and a plurality of struts extending between the first ring and the second ring around the periphery of the rings, each of the struts being angled to the axial direction of the ring.

Preferably the plurality of struts are formed from a continuous piece of material and the first and second rings are also formed from the continuous piece of material.

Preferably there are bends between adjacent struts or there is a bend, a circumferential portion extending around the respective ring and another bend between adjacent struts.

U.S. Pat. No. 5,387,235 entitled "Expandable Transluminal Graft Prosthesis For Repair Of Aneurysm" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Barb and Expandable Transluminal Graft Prosthesis For Repair of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

PCT Patent Publication No. WO 98/53761 entitled "A Prosthesis And A Method And Means Of Deploying A Prosthesis" discloses an introducer for a prosthesis which retains the prosthesis so that each end can be moved independently. These features and other features disclosed in PCT Patent Publication No. WO 98/53761 could be used with the present invention and the disclosure of PCT Patent Publication No. WO 98/53761 is herewith incorporated in its entirety into this specification.

U.S. Pat. No. 6,524,335 and PCT Patent Publication No. WO 99/29262 entitled "Endoluminal Aortic Stents" disclose a fenestrated prosthesis for placement where there are intersecting arteries. This feature and other features disclosed in U.S. Pat. No. 6,524,335 and PCT Patent Publication No. WO 99/29262 could be used with the present invention and the disclosure of U.S. Pat. No. 6,524,335 and PCT Patent Publication No. WO 99/29262 is herewith incorporated in its entirety into this specification.

U.S. patent application Ser. No. 10/280,486, filed Oct. 25, 2002 and published on May 8, 2003 as U.S. Patent Application Publication No. US-2003-0088305-A1 and PCT Patent Publication No. WO 03/034948 entitled "Prostheses For Curved Lumens" discloses prostheses with arrangements for bending the prosthesis for placement into curved lumens. This feature and other features disclosed in U.S. patent application Ser. No. 10/280,486, and U.S. Patent Application Publication No. US-2003-0088305-A1 and PCT Patent Publication No. WO 03/034948 could be used with the present invention and the disclosure of U.S. patent application Ser. No. 10/280,486, and U.S. Patent Application Publication No. US-2003-0088305-A1 and PCT Patent Publication No. WO 03/034948 is herewith incorporated in its entirety into this specification.

U.S. Provisional Patent Application Ser. No. 60/392,682, filed Jun. 28, 2002, and U.S. patent application Ser. No. 10/447,406, filed May 29, 2003, and Published on Dec. 18, 2003, as US Patent Application Publication No. US-2003-0233140-A1 entitled "Trigger Wires" disclose release wire systems for the release of stent grafts retained on introducer devices. This feature and other features disclosed in U.S. Provisional Patent Application Ser. No. 60/392,682 and U.S. patent application Ser. No. 10/447,406, filed May 29, 2003 could be used with the present invention and the disclosure of U.S. Provisional Patent Application Ser. No. 60/392,682 and U.S. patent application Ser. No. 10/447,406, filed May 29, 2003 are herewith incorporated in their entirety into this specification.

U.S. Provisional Patent Application Ser. No. 60/392,667, filed Jun. 28, 2002, and U.S. patent application Ser. No. 10/609,846, filed Jun. 30, 2003, and Published on May 20, 2004, as US Patent Application Publication No. US-2004-0098079-A1, and PCT Patent Publication No. WO 2004/028399 entitled "Thoracic Deployment Device" disclose introducer devices adapted for deployment of stent grafts particularly in the thoracic arch. This feature and other features disclosed in U.S. Provisional Patent Application Ser. No. 60/392,667, U.S. patent application Ser. No. 10/609,846, and US Patent Application Publication No. US-2004-0098079-A1, and PCT Patent Publication No. WO 2004/028399 could be used with the present invention and the disclosure of U.S. Provisional Patent Application Ser. No. 60/392,667, U.S. Patent application Ser. No. 10/609,846, and US Patent Application Publication No. US-2004-0098079-A1, and PCT Patent Publication No. WO 2004/028399 is herewith incorporated in its entirety into this specification.

U.S. Provisional Patent Application Ser. No. 60/392,599, filed Jun. 28, 2002, and U.S. patent application Ser. No. 10/609,835, filed Jun. 30, 2003, and published on Jun. 3, 2004, as U.S. Patent Application Publication No. US-2004-0106978-A1, and PCT Patent Publication No. WO 2004/002370 entitled "Thoracic Aortic Aneurysm Stent Graft" disclose stent grafts that are useful in treating aortic aneurysms particularly in the thoracic arch. This feature and other features disclosed in U.S. Provisional Patent Application Ser. No. 60/392,599, U.S. patent application Ser. No. 10/609,835, and U.S. Patent Application Publication No. US-2004-0106978-A1, and PCT Patent Publication No. WO 2004/002370 could be used with the present invention, and the disclosure of U.S. Provisional Patent Application Ser. No. 60/392,599, U.S. patent application Ser. No. 10/609,835, and U.S. Patent Application Publication No. US-2004-0106978-A1, and PCT Patent Publication No. WO 2004/002370 is herewith incorporated in its entirety into this specification.

U.S. Provisional Patent Application Ser. No. 60/391,737, filed Jun. 26, 2002, U.S. patent application Ser. No. 10/602,930, filed Jun. 24, 2003, and published on Mar. 18, 2004, as U.S. Patent Application Publication No. US-2004-0054396-A1, and PCT Patent Publication No. WO 2004/002365 entitled "Stent-Graft Fastening" disclose arrangements for fastening stents onto grafts particularly for exposed stents. This feature and other features disclosed in U.S. Provisional Patent Application No. 60/391,737, U.S. patent application Ser. No. 10/602,930, and U.S. Patent Application Publication No. US-2004-0054396-A1, and PCT Patent Publication No. WO 2004/002365 could be used with the present invention and the disclosure of U.S. Provisional Patent Application Ser. No. 60/391,73, U.S. patent application Ser. No. 10/602,930, and U.S. Patent Application Publication No. US-2004-0054396-A1, and PCT Patent Publication No. WO 2004/002365 is herewith incorporated in its entirety into this specification.

U.S. Provisional Patent Application Ser. No. 60/405,367, filed Aug. 23, 2002, U.S. patent application Ser. No. 10/647,642, filed Aug. 25, 2003, and published on Apr. 15, 2004, as U.S. Patent Application Publication No. US-2004-0073289-A1, and PCT Patent Publication No. WO 2004/017868 entitled "Asymmetric Stent Graft Attachment" disclose retention arrangements for retaining onto and releasing prostheses from introducer devices. This feature and other features disclosed in U.S. Provisional Patent Application Ser. No. 60/405,367, filed Aug. 23, 2002, U.S. patent application Ser. No. 10/647,642, filed Aug. 25, 2003, and U.S. Patent Application Publication No. US-2004-0073289-A1, and PCT Patent Publication No. WO 2004/017868 could be used with the present invention and the disclosure of U.S. Provisional Patent Application Ser. No. 60/405,367, filed Aug. 23, 2002, U.S. patent application Ser. No. 10/647,642, filed Aug. 25, 2003, and U.S. Patent Application Publication No. US-2004-0073289-A1, and PCT Patent Publication No. WO 2004/017868 is herewith incorporated in its entirety into this specification.

U.S. patent application Ser. No. 10/322,862, filed Dec. 18, 2002 and published as Publication No. US2003-0120332, and PCT Patent Publication No. WO03/053287 entitled "Stent Graft With Improved Adhesion" disclose arrangements on stent grafts for enhancing the adhesion of such stent grafts into walls of vessels in which they are deployed. This feature and other features disclosed in U.S. patent application Ser. No. 10/322,862, filed Dec. 18, 2002 and published as Publication No. US2003-0120332, and PCT Patent Publication No. WO03/053287 could be used with the present invention and the disclosure of U.S. patent application Ser. No. 10/322,862, filed Dec. 18, 2002 and published as Publication No. US2003-0120332, and PCT Patent Publication No. WO03/053287 are herewith incorporated in its entirety into this specification.

U.S. Provisional Patent Application Ser. No. 60/405,769, filed Aug. 23, 2002, U.S. patent application Ser. No. 10/645,095, filed Aug. 23, 2003, and published on Apr. 29, 2004, as U.S. Patent Application Publication No. US-2004-0082990-A1, and PCT Patent Publication No. WO 2004/017867 entitled "Composite Prostheses" discloses prostheses or stent grafts suitable for endoluminal deployment. These prostheses and other features disclosed in U.S. Provisional Patent Application Ser. No. 60/405,769, U.S. patent application Ser. No. 10/645,095, and U.S. Patent Application Publication No. US-2004-0082990-A1, and PCT Patent Publication No. WO 2004/017867 could be used with the present invention and the disclosure of U.S. Provisional Patent Application Ser. No. 60/405,769, U.S. patent application Ser. No. 10/645,095, and U.S. Patent Application Publication No. US-2004-0082990-A1, and PCT Patent Publication No. WO 2004/017867 is herewith incorporated in its entirety into this specification.

BRIEF DESCRIPTION OF THE DRAWING

This then generally describes the invention but to assist at understanding, reference will now be made to the accompanying drawings which show some preferred embodiments of the invention.

In the drawings.

DETAILED DESCRIPTION

Figure 1:
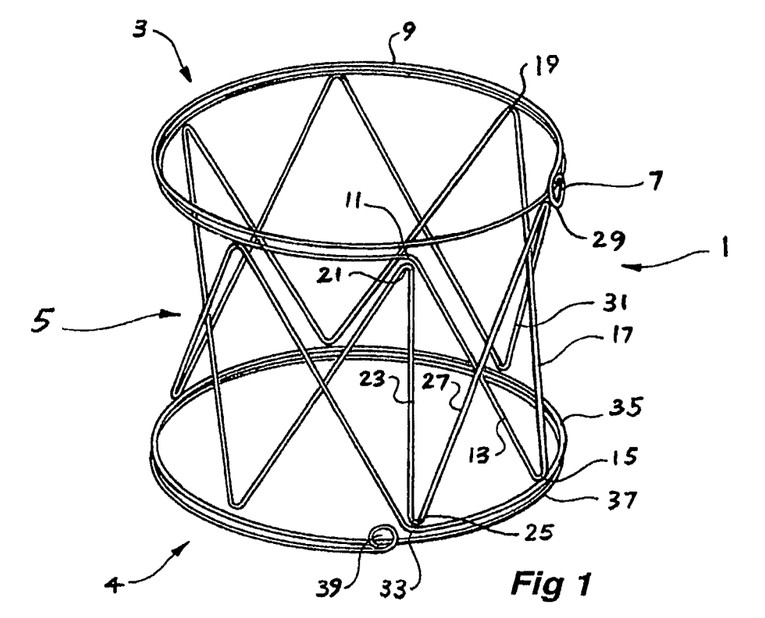
FIG. 1 shows a perspective view of a first embodiment of stent according to this invention.

Now looking more closely at the drawings and in particular FIG. 1, it will be seen that the stent 1 according to one embodiment of this invention comprises a first resilient ring assembly 3 and a second resilient ring assembly 4 spaced (preferably parallel) to and axially away from the first ring assembly 3 and a number of zig zag struts 5 between the first resilient ring assembly 3 and the second resilient ring assembly 4. The first and second resilient ring assemblies and the struts comprise a metallic wire.

Although metal or metal alloy materials are preferred other resilient materials such as polymers, carbon fibres and other biocompatible materials are also contemplated.

The first ring assembly 3 commences at a loop 7 of the wire and is formed from two circles or turns of wire 9 and then at 11 there is a bend and the wire is angled in a first strut 13 extending to a bend 15 adjacent the second ring assembly 4 and then a further angled strut 17 to a bend 19 adjacent the first ring assembly 3. Consecutive angled struts and bends extend around the periphery of the ring assembly 3 and the ring assembly 4 from the bend 19 until bend 21 adjacent to the bend 11 where there is an axial strut 23 extending to the second ring assembly 4 and a bend 25. From the bend 25 is an angled strut 27 which extends to the first ring assembly 3 where there is a bend 29 and a subsequent angled strut 31. Subsequent angled struts and bends extend around the periphery of the second ring assembly 4 and first the ring assembly 3 from strut 31 to a bend 33 adjacent to bend 25 where the wire extends to a first circle or turn 35 of the ring assembly 4 and then to a second turn 37 of the ring assembly 4 to finally terminate in a loop 39 of the wire.

The wire in this embodiment is preferably nitinol and has a diameter of 150 microns and the stent has a diameter of 8 mm and a length of 9 mm. There are three sets of struts with a bend between them extending from each of the rings to the other of the rings giving a total of twelve angled struts and one axial strut.

By this arrangement a stent with good radial dimensional stability is formed because the rings restrict radial expansion and contraction but being formed from resilient wire has good compressibility to enable it to be deployed endoluminally in a contracted state.

Figure 2:
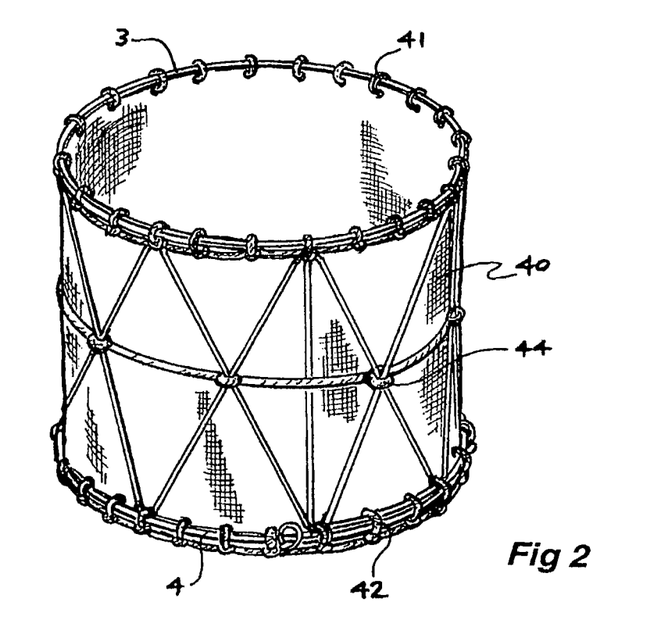
FIG. 2 shows the stent of the embodiment of FIG. 1 with an internal covering of a biocompatible graft material.

FIG. 2 shows an embodiment of the stent shown in FIG. 1 with a biocompatible graft material lining. The graft material 40 is retained by stitching 41 to the first ring assembly 3 and by stitching 42 to the second ring assembly 4. Stitching 44 is also provided to retain the graft material into a cylindrical shape where the struts cross between the first and second rings. By this arrangement a portion of stent graft is formed which has good dimensional stability and which may be mounted to or provided on the end of a stent graft, on the leg of a stent graft, or as or on a side arm from a stent graft.

The graft material may be Dacron, Thoralon™ material, nylon or any other suitable material such as collagenous extracellular matrix (ECM) material including small intestine submucosa, which is commercially available from Cook Biotech, West Lafayette, Ind., USA.

Figure 3:
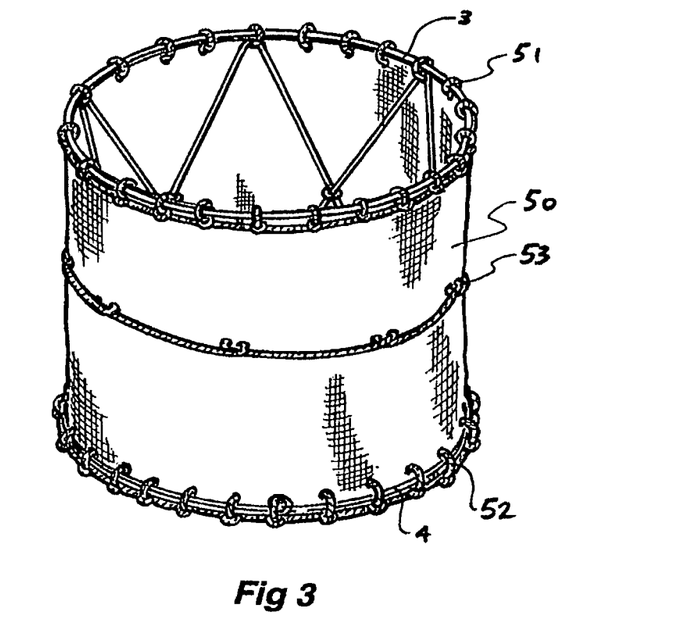
FIG. 3 shows the stent of the embodiment of FIG. 1 with an external covering of a biocompatible graft material.

Similarly in FIG. 3 a biocompatible graft material covering 50 is provided on the outside of the stent 1 with the material 50 sewn to and retained onto the first ring assembly 3 by stitching 51, onto the second ring assembly 4 by stitching 52 and to the struts by stitching 53.

Figure 4:
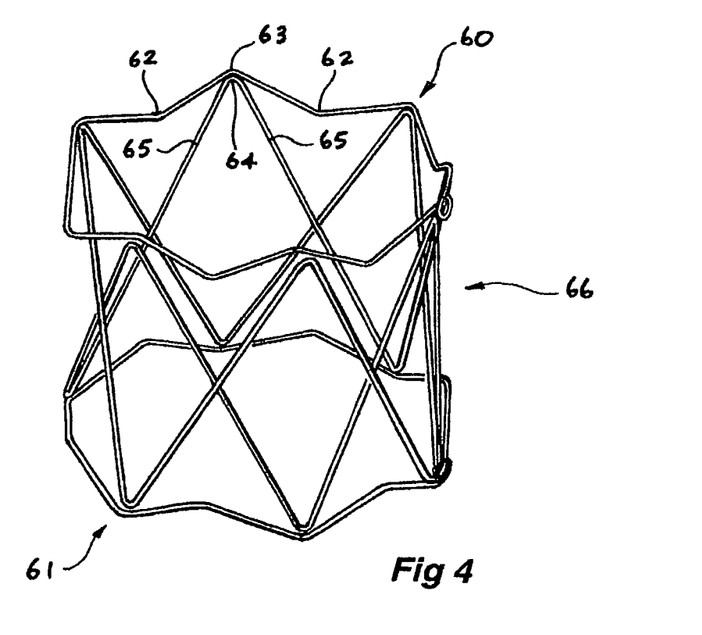
FIG. 4 shows an alternative embodiment of a stent according to this embodiment.

FIG. 4 shows a further embodiment of a stent according to this invention. In this embodiment the first ring 60 and the second ring 61 of the stent are formed as a wavy ring with the waves extending axially so that there are alternate troughs 62 and crests 63. The crests 63 correspond substantially with the bends 64 between struts 65 of the zig zag portion 66 of the stent. The apices 62 extend towards the ring 61

The wavy rings can be formed so that their rest diameter is substantially the desired final diameter of the stent.

These wavy rings, while still providing good dimensional stability, allow radial compression of the rings 60 and 61 as well as the zig zag portion 66. This will assist with enabling this form of the stent to be radially compressed onto a delivery device as required.

Figure 5:
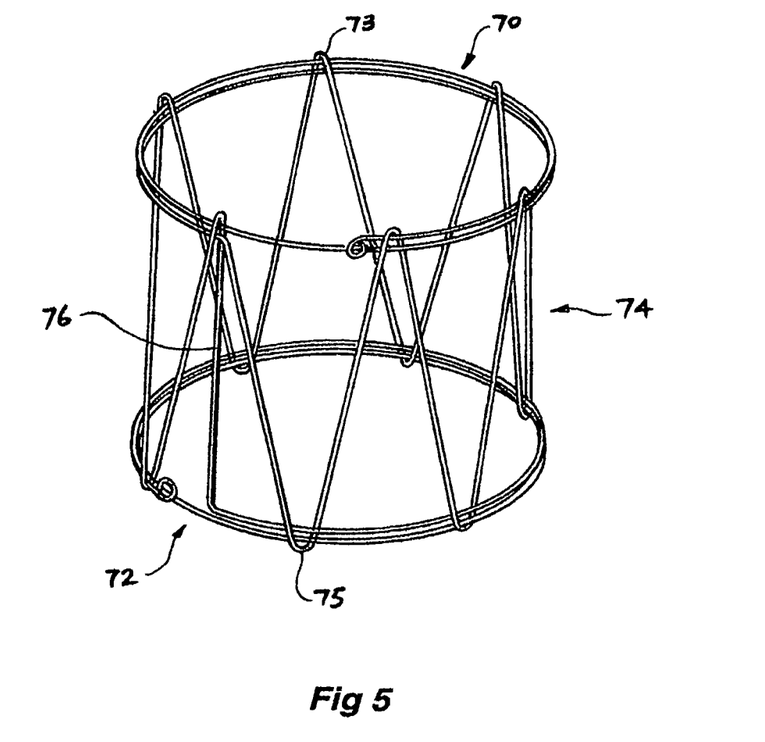
FIG. 5 shows a still further embodiment of a stent according to this invention.

FIG. 5 shows a still further embodiment of a stent according to this invention. In this embodiment, the stent has a two-circle or turn ring 70 of wire at its upper end, a two-circle or turn ring 72 of wire at its lower end and a number of zig zag struts 74 of wire between the rings 70 and 72. In this embodiment, however, all of the pairs of struts commence at the ring 70 and after six pairs of zig zag struts, a single strut 76 extends to the ring 72 to complete the stent with the two turns of the second ring. Rather than the axial strut 76 there may be a further angled strut between the first ring 70 and the second ring 72. In this embodiment the bends 73 incorporate the ring 70 within the acute angle of the bend and the bends 75 incorporate the ring 72 within the acute angle of the bend.

Figure 6:
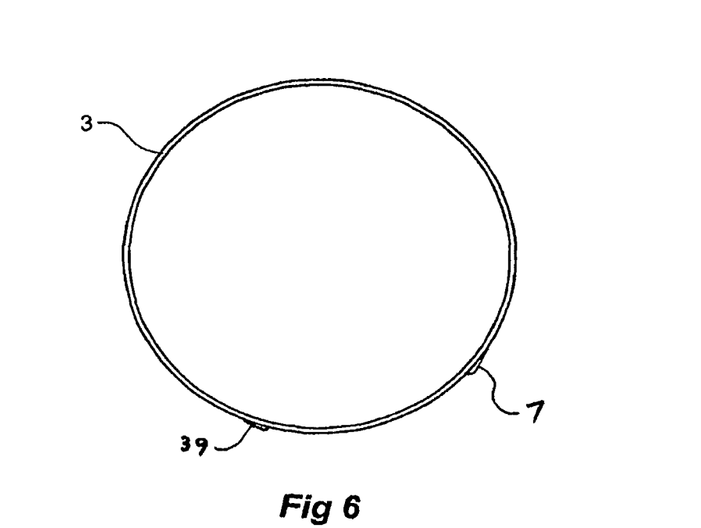
FIG. 6 shows a plan view of a stent according to this invention.

FIG. 6 shows a plan view of the stent shown in FIG. 1 and it will be noted that the stent in plan view is substantially cylindrical and the ring 3 and the termination loops 7 and 39 can be seen.

Figure 7:
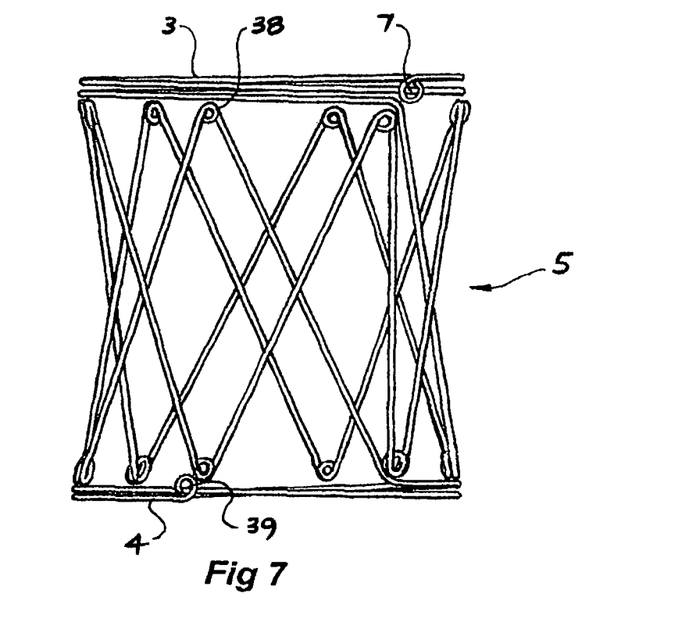
FIG. 7 shows a side elevation of a stent according to this invention.

FIG. 7 shows a side elevation view of the stent similar to that shown in FIG. 1 except that at the apex of each of the bends there is a helix arrangement 38 to give more resilience to each bend. It will be noted that the zig zag struts 5 provide an essentially cylindrical peripheral surface to the stent.

Figure 8:
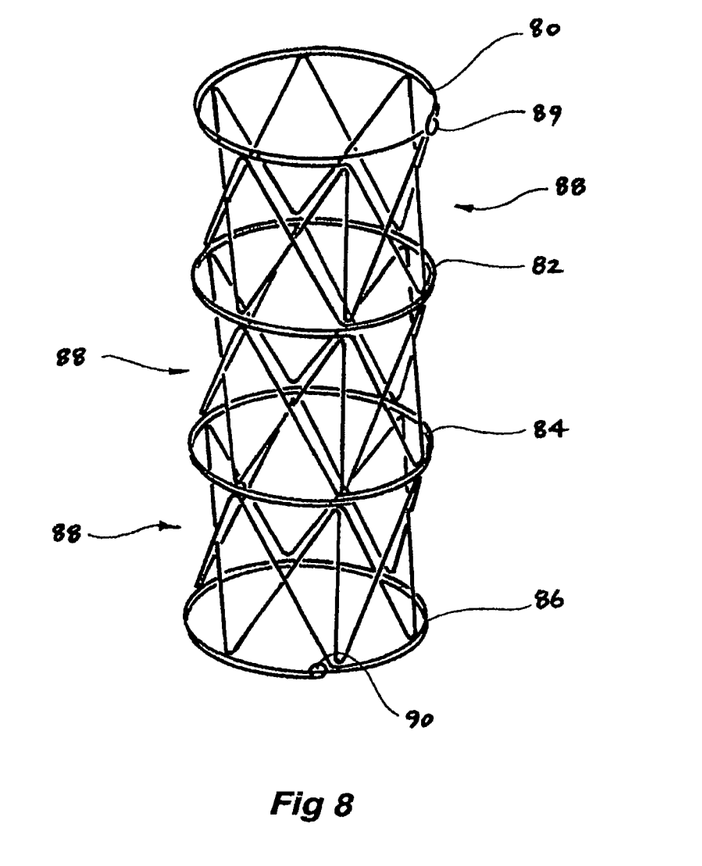
FIG. 8 shows an embodiment of a stacked stent according to this invention.

FIG. 8 shows a further embodiment of a stent in which there is a first ring 80, a second ring 82, a third ring 84 and a fourth ring 86. Between each pair of rings there is a zig zag strut portion 88. The stent according to this embodiment of the invention can be made from a single length of wire commencing with the loop 89 on the ring 80 and terminating with the loop 90 on the ring 86.

By this arrangement, a substantially cylindrical elongated stent can be formed without welds which could introduce weakness into the stent.

Figure 9:
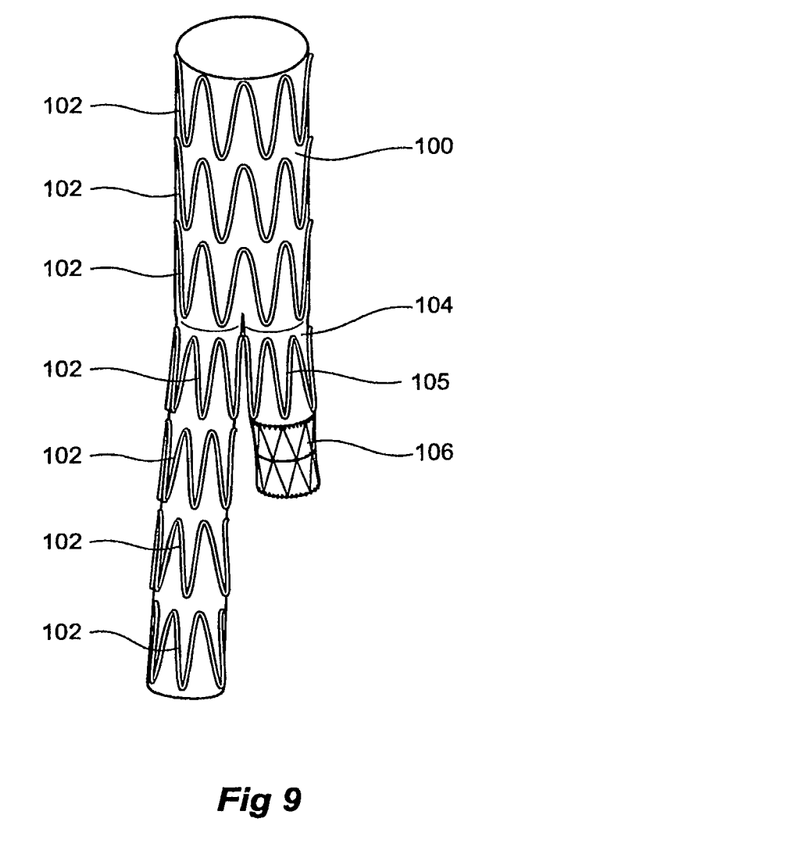
FIG. 9 shows an embodiment of this invention used as a stent on the end of a leg of a bifurcated stent graft.

FIG. 9 shows an arrangement of bifurcated or branched stent graft according to this invention using a stent of the present invention.

The stent graft comprises a tubular main body 100 with well-known Gianturco type zig zag Z stents 102 along its length. Extending from a bifurcation 103 in the tubular body 100 is a side arm 104. The side arm 104 has a Gianturco type zig zag Z stent 105 and terminates in a ring stent 106 of the type disclosed in this invention. The use of the stent graft 106 on the side arm 104 provides a diametrically stable arm into which an extension leg or arm can be inserted with good reliability for sealing into the side arm either using a covered self expanding stent or a covered balloon expandable stent.

Figure 10:
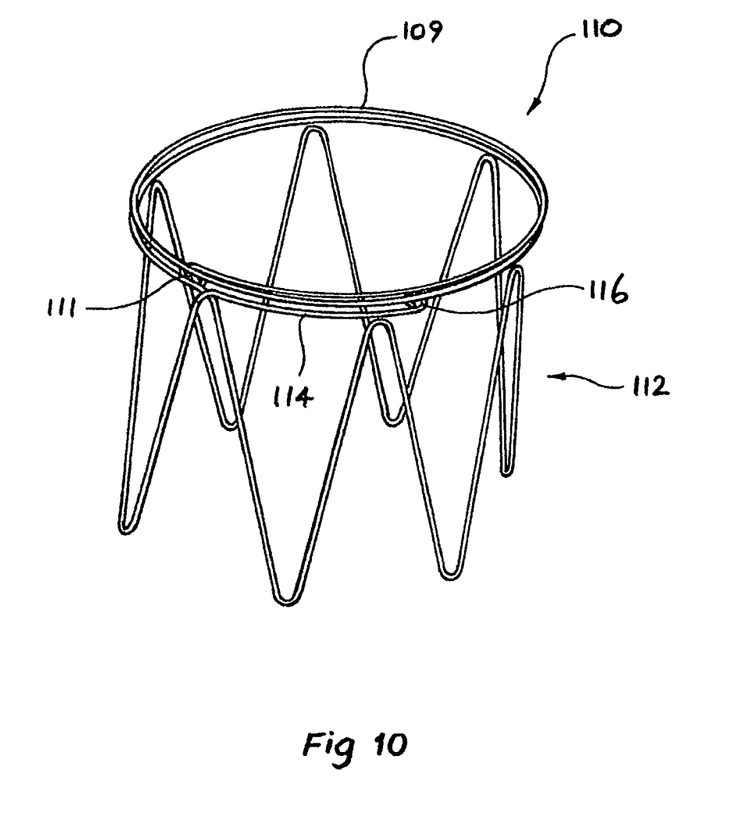
FIG. 10 shows a perspective view of a alternative embodiment of the invention.

FIG. 10 shows a perspective view of a still further embodiment of a stent according to this invention. In this embodiment, the stent has two circles or turns of wire 109 starting with a loop 111 to form a ring assembly 110 of wire at its upper end and a number of zig zag struts 112 of wire extending axially from the circumference of the rings 110. In this embodiment, however, all of the pairs of struts 112 commence at the ring 110 and after six pairs of zig zag struts 112 a partial turn of wire 114 follows the ring 110 and terminates in a loop 116 to complete the stent. The stent of this embodiment may be particularly useful for mounting onto a leg or arm of a stent graft to provide dimensional stability at its end.

Figure 11:
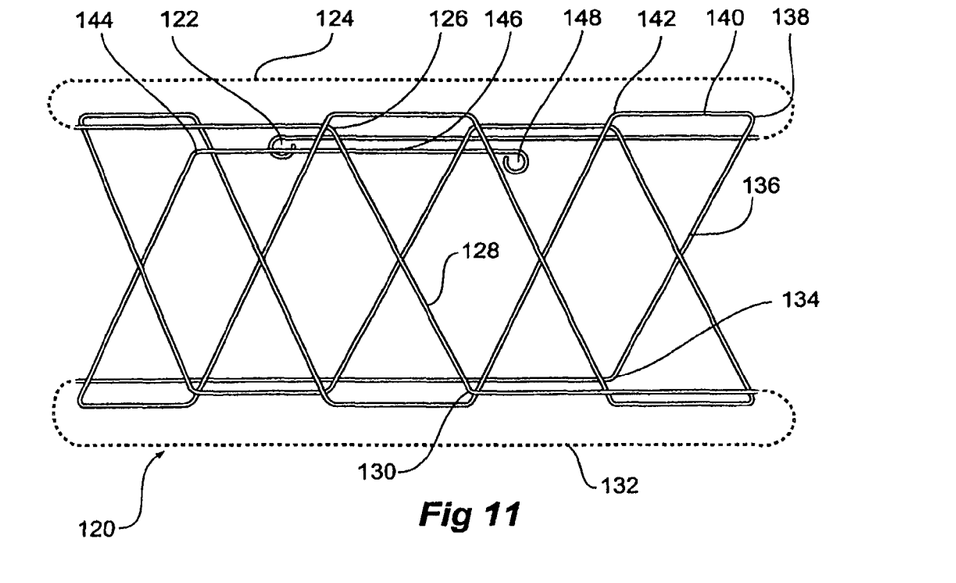
FIG. 11 shows a developed view of a further alternative embodiment of the invention.
Figure 12:
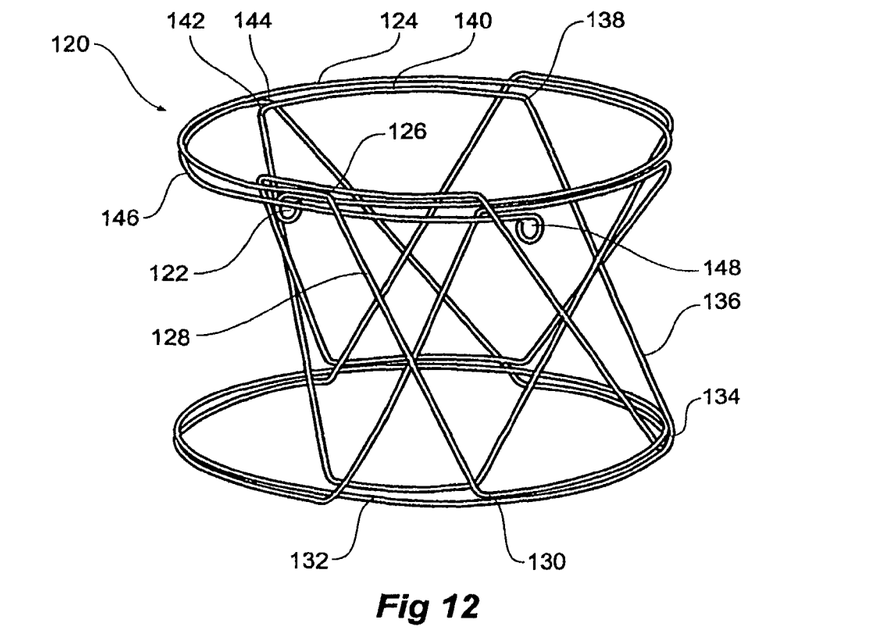
FIG. 12 shows a perspective view of the alternative embodiment of the invention shown in FIG. 11.

FIG. 11 and FIG. 12 show a further alternative embodiment of the invention.

FIG. 11 shows a stylised or developed view of a stent according to an embodiment of the invention laid out flat to show the continuous strand of Nitinol or stainless steel formed into the rings and struts. FIG. 12 shows the stent of FIG. 11 in a perspective view. In this embodiment there are in effect five sets of bends at each ring of the stent but there may be other odd numbers of sets of bends such as seven or nine.

The stent 120 of this embodiment has a single continuous length of material such as wire starting at loop 122 and forming a first ring 124 to a bend 126 and then a first angled strut 128 to another bend 130 and then into a second ring 132 which is spaced apart, essentially coaxial with and parallel to the first ring 124. The second ring 132 has one and one fifth turns and then a bend 134 and then an angled strut 136 to the first ring and a bend 138. Beyond the bend 138 there is a circumferential peripheral portion 140 essentially parallel and adjacent to the first ring 124 to a further bend 142. There are then alternate struts and peripheral portions with bends in between them of the continuous length of material making a total of ten struts in all ending with bend 144. After the bend 144 the continuous length of material extends in a circumferential peripheral portion 146 essentially parallel and adjacent to the first ring 124 to a terminal loop 148. It will be noted that by this arrangement there is at all portions of each ring at least two portions of the wire or other continuous material.

By the arrangement of this embodiment of the invention the sharp bends of the earlier embodiments between the zig zag struts do not exist and the short peripheral portions between bends become part of the ring and can be sutured to graft material making a more secure structure.

Figure 13:
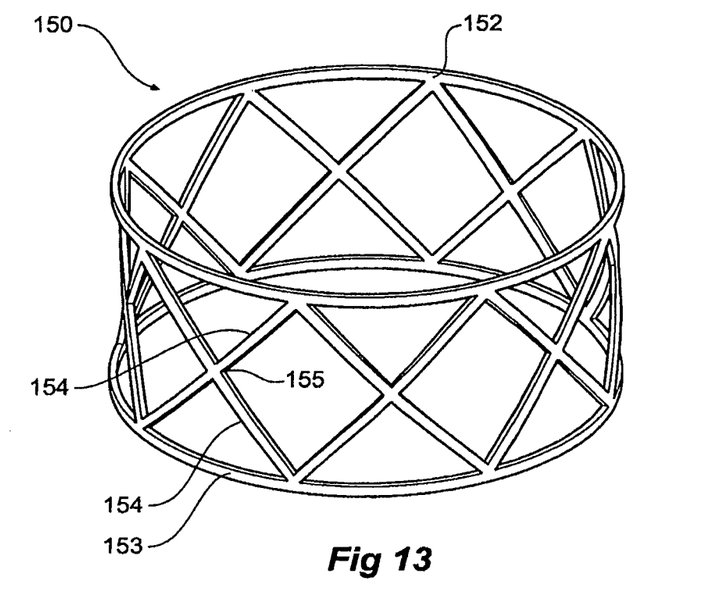
FIG. 13 shows a perspective view of the alternative embodiment of the invention.

FIG. 13 shows a perspective view of the alternative embodiment of the invention. In this embodiment the stent 150 is formed from a tube or cannula of metal or other material and can be, for instance, laser cut from the tube or cannula in a known manner. The material of the stent 150 is resilient so that the stent is deformable.

The stent 150 includes a first resilient ring 152 and a second resilient ring 153 spaced apart axially from the first ring 152, and a plurality of diagonal or zig zag struts 154 around the periphery and between the first and second resilient rings. In this embodiment the struts 154 meet in between the first and second rings at 155 but in an alternative embodiment the struts may not cross between the first and second rings. FIG. 13 shows a squat ring stent according to the invention, that is, the height is about half the diameter.

Figure 14:
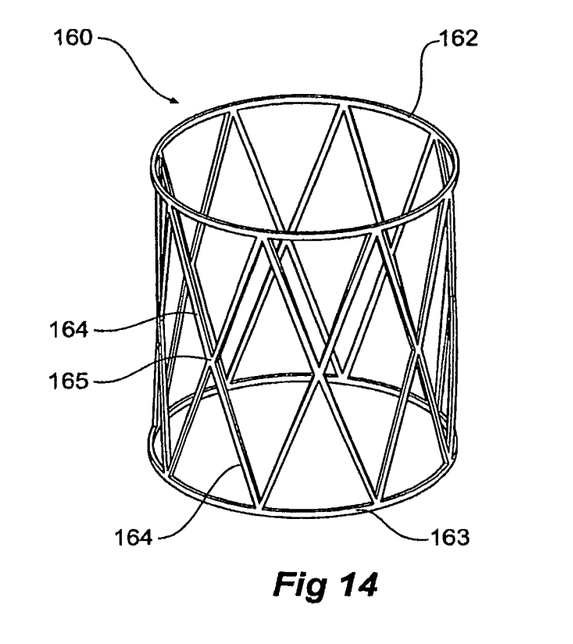
FIG. 14 shows a perspective view of the further embodiment of the invention.

FIG. 14 shows a perspective view of the alternative embodiment of the invention. In this embodiment the ring stent is formed from a tube or cannula of metal or other material and can be, for instance, laser cut from the tube or cannula in a known manner. The material of the stent 160 is resilient so that the stent is deformable.

The ring stent includes a first resilient ring 162 and a second resilient ring 163 spaced apart axially from the first ring 162, and a plurality of diagonal or zig zag struts 164 around the periphery and between the first and second resilient rings. The struts cross between the first ring 162 and second ring 163 to form junctions 165. In this embodiment the ring stent is tall rather than squat, that is, the height is about twice the diameter.

Throughout this specification various indications have been given as to the scope of the invention but the invention is not limited to any one of these but may reside in two or more combined together. The examples are given for illustration only and not for limitation.

What is claimed is:

1. A stent arrangement comprising a first resilient planar wire ring and a second resilient planar wire ring, the second ring being substantially parallel to and spaced axially apart from the first ring and an undulating ring extending between the rings and around the periphery of a least one of the first ring and second ring, wherein the undulating ring has a series of proximal and distal apices, wherein each of the resilient planar rings comprises a continuous ring of wire separated from the proximal and distal apices and wherein each of the rings comprises a free terminal end.

2. A stent arrangement as in claim 1 wherein at least one of the first ring and the second ring comprises a metallic material.

3. A stent arrangement as in claim 1 wherein the first ring and the second ring comprise at least one of a wire and a metal cannula.

4. A stent arrangement as in claim 3 wherein terminal ends in each ring is provided with a loop, whereby the stent does not present a pointed end which could damage a vessel.

5. A stent arrangement as in claim 1 wherein at least one of the first ring and the second ring and undulating ring comprise a single piece of wire.

6. A stent arrangement as in claim 1 wherein a single undulating ring is disposed between the first ring and the second ring.

7. A stent arrangement as in claim 1 wherein the first ring and second ring each includes first and second turns of wire.

8. A stent arrangement as in claim 1 wherein the first ring is adjacent the proximal apices of the undulating ring and the second ring is spaced apart from the first ring and adjacent the distal apices of the undulating ring.

9. A self-expanding stent arrangement comprising a first planar ring of a portion of wire and an undulating ring having proximal and distal apices a extending axially from and around a periphery of the first planar ring, wherein the first planar ring comprises a continuous ring of wire separated from the proximal and distal apices and wherein the first planar ring comprises a free terminal end, wherein the first planar ring is adjacent the proximal apices of the undulating ring and a second ring is spaced apart from the first planar ring and adjacent the distal apices of the undulating ring.

10. A stent arrangement as in claim 9 wherein the ring and the undulating ring comprise a single piece of wire.

11. A stent arrangement as in claim 9 wherein one of the proximal and distal apices are adjacent the ring.

12. A stent arrangement as in claim 9 wherein there are at least two turns of wire in the ring.

13. A stent arrangement as in claim 9 wherein the terminal end of the wire in the ring includes a loop, such that the stent does not present a pointed end of wire which could damage a vessel into which it is deployed.

14. A stent arrangement as in claim 9 wherein there are at least two turns of wire in the second ring and a terminal end of the wire in the second ring includes a loop so that the stent does not present a pointed end of wire which could damage a vessel.

15. A self-expanding stent arrangement comprising a first planar ring formed from at least two turns of a wire and having a terminal free end ending in a loop, a second planar ring formed from at least two turns of a wire and having a terminal free end ending in a loop, the second ring defining a plane which is substantially parallel to and spaced axially apart from the plane of the first ring, and an undulating ring having proximal and distal apices extending between and around the periphery of the first and second rings, wherein at least one of the proximal apices and one of the distal apices are not attached to the first and second rings, and wherein each of the resilient planar rings comprises a continuous ring of wire separated from the proximal and distal apices.

16. A stent arrangement as in claim 15 wherein the stent is in a substantially cylindrical or drum form and is covered or lined with a biocompatible graft material.

* * * * *